US006486204B2

(12) United States Patent
Waldstreicher et al.

(10) Patent No.: US 6,486,204 B2
(45) Date of Patent: Nov. 26, 2002

(54) TREATMENT OR PREVENTION OF PROSTATE CANCER WITH A COX-2 SELECTIVE INHIBITING DRUG

(75) Inventors: Joanne Waldstreicher, Scotch Plains, NJ (US); Briggs W. Morrison, Watchung, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/771,315

(22) Filed: Jan. 26, 2001

(65) Prior Publication Data

US 2001/0047022 A1 Nov. 29, 2001

Related U.S. Application Data

(60) Provisional application No. 60/178,722, filed on Jan. 28, 2000.

(51) Int. Cl.$^7$ .............................................. A61K 31/34
(52) U.S. Cl. ..................... 514/473; 514/284; 514/458
(58) Field of Search ................... 514/473, 284, 514/458

(56) References Cited

U.S. PATENT DOCUMENTS

| | | | |
|---|---|---|---|
| 5,935,990 A | | 8/1999 | Khanna et al. |
| 5,972,968 A | | 10/1999 | Seibert et al. |
| 6,020,343 A | * | 2/2000 | Belley et al. ............... 514/309 |
| 6,258,824 B1 | * | 7/2001 | Yang .......................... 514/312 |
| 6,319,910 B1 | * | 11/2001 | Amin et al. ................ 514/152 |
| 6,326,507 B1 | * | 12/2001 | Gribble et al. .............. 514/519 |

OTHER PUBLICATIONS

Urology (United States) Feb 1999, 53 (2) pp. 440–445, Goluboff, E. T., et al.
International Journal of Cancer 77 (4) pp. 511–515, Aug. 12, 1998, Norrish, Alan, et al.
Int. J. Cancer (United States) Apr. 15, 1994, (2) p. 176–80, Chaudry, A. A., et al.
Anticancer Res (Greece) Nov.–Dec. 1994, 4 (6) p. 391–4, Drago, J. R., et al.
British Journal of Cancer 75 (8): pp. 1111–1118, 1997 Tjandrawinata, R. R., et al.
The Journal of Urology, vol. 164, 820–825, Sep. 2000, Liu, X., et al.
Adv Exp Med. Bio (United States 1997, 407 p. 163–70, Tjandrawinata, R. R. et al.
Journal of Investigation Medicine 44 (1): pp. 128A 1996, Tjandrawinata, R. R., et al.
FEBS Lett (Netherlands) Sep. 13 1993, 330 (2) p. 156–60, O'Neill, G. P., et al.
Proceedings of the American Association for Cancer Research Annual Meeing 40 pp. 4–5, Mar. 1999, Piazza, G. a., et al.
Proceedings of the American Association for Cancer Research Annual Meeting 39 pp. 132–133, Mar. 1998, Freije, D., et al.
Cancer Res (United States) Oct. 1, 1998, 58 (19) p. 4245–9, Liu, Y. H., et al.
Journal of Urology 161 (4 SUPPL.) p. 61, Apr. 1999; Levine Alcie, et al.
Journal of Urology 161 (4 SUPPL.) p. 134, Apr. 1999; Kirschenbaun, Alexander, et al.
Proceedings of the American Association for Cancer Research Annual Meeing, 40 p. 563, Mar. 1999, Attiga, F. A. et al.
Proceedings of the American Association for Cancer Research Annual Meeting 40 p. 366, Mar., 1999, Jean–Jacque Jims, et al.
Clinical and Experimental Metastasis, pp. 687–694, 1999, Liu, X. H., et al.
Medline on Stn. No. 20047123, Prostate, vol. 42, No. 1, pp. 73–78, 2000, Gupta, et al.09/771.
Proceedings of the American Association for Cancer Research Annual Meeting 40p. 414 Mar. 1999; Liu X. H.

* cited by examiner

*Primary Examiner*—James H. Reamer
(74) *Attorney, Agent, or Firm*—Raynard Yuro; David L. Rose

(57) ABSTRACT

A COX-2 selective inhibiting drug is disclosed as useful in treating or preventing prostate cancer. The compound is used alone or in combination with other drugs.

10 Claims, No Drawings

TREATMENT OR PREVENTION OF PROSTATE CANCER WITH A COX-2 SELECTIVE INHIBITING DRUG

CROSS REFERENCE TO RELATED APPLICATIONS

This application claims the benefit of U.S. Provisional Application No. 60/178,722, filed on Jan. 28, 2000.

BACKGROUND OF THE INVENTION

The present invention relates to the treatment or prevention of prostate cancer using cyclooxygenase-2 (COX-2) selective inhibiting drugs. Prostate cancer is the most common form of malignancy and second leading cause of cancer-related deaths among men in the United States. While conventional therapy for advanced prostate cancer can be paliative, patients having advanced prostate cancer generally relapse over time.

Cyclooxygenase-2 is a key enzyme in the conversion of arachidonic acid to prostaglandins and other eicosanoids. Cyclooxygenase-2 is the inducible form of the enzyme, cyclooxygenase-1 being constitutively expressed in many tissues and cell types.

Cyclooxygenase-2 expression can be induced by a variety of factors, including, for example, growth factors, interleukin-1 and tumor promoting factors. The enzyme is expressed in a number of tumor cells, and human cancers, among which is prostate cancer.

One object of the present invention is to provide a method of treating or preventing prostate cancer using a cyclooxygenase-2 selective inhibiting drug.

Another object of the present invention is to provide a treatment and prevention modality that is less toxic than conventional cancer chemotherapy, and less debilitating than conventional radiation therapy.

Another object is to provide a treatment and prevention means that is readily combinable with other treatment modalities such as radiation therapy, hormonal therapy, and surgery. These and other objects will be apparent to those of ordinary skill from the teachings herein.

SUMMARY OF THE INVENTION

A method of treating or preventing prostate cancer in a mammalian male patient in need thereof, comprising administering to said patient an amount of rofecoxib that is effective for treating or preventing prostate cancer.

DESCRIPTION OF THE INVENTION

In one aspect of the invention, a method of treating or preventing prostate cancer in a mammalian male patient in need thereof is addressed that is comprised of administering to said patient an amount of rofecoxib that is effective for treating or preventing prostate cancer.

In another aspect of the invention, a method of treating or preventing prostate cancer in a mammalian male patient in need thereof is addressed that is comprised of administering to said patient an amount of rofecoxib that is effective for treating or preventing prostate cancer in combination with at least one member selected from the compounds described below.

As used herein, prostate cancer is defined as present in male patients having malignant cells that are derived from the prostate, which can be detected or confirmed via ultrasound guided biopsy of the prostate tissue, transurethral prostatectomy (TURP), biopsy of a metastatic tumor and the like.

The COX-2 selective inhibiting compound may be administered in combination with one or more conventional agents or treatment modalities. For example, the compound rofecoxib can be used to treat or prevent prostate cancer in conjunction with type 1, type 2 or dual type1/type 2 5-alpha reductase inhibitors. Examples of 5-alpha reductase inhibitors include finasteride, dutasteride and epristeride. The doses of these 5-alpha reductase inhibiting compounds are conventional, and are determined by the skilled clinician.

The COX-2 selective inhibiting compound may likewise be administered in conjunction with radiation therapy, such as external radiation or radioactive seed implantation.

The COX-2 selective inhibiting compound may alternatively be administered in conjunction with selenium. Typical dosages of selenium range from about 25 mcg to about 1 mg. More particularly, the dosages of selenium range from about 50 mcg to about 200 mcg.

The COX-2 selective inhibiting compound may alternatively be administered in conjunction with vitamin C and/or vitamin E. Typical dosages of vitamins C and E are well known.

The COX-2 selective inhibiting compound may alternatively be administered in conjunction with farnesyl protein transferase inhibitors. Numerous farnesyl protein transferase inhibitors are known in the scientific and patent literature.

The COX-2 selective inhibiting compound may alternatively be administered in conjunction with one or more conventional anti-cancer agents. Examples of such conventional anti-cancer agents include, for example, alkylating agents, antibiotics, hormones, anti-hormones, LHRH analogs and antagonists, anti-metabolites, monoclonal antibodies, topoisomerase I inhibitors, topoisomerase II inhibitors, and miscellaneous anti-cancer agents. Examples of alkylating agents that may be used in conjunction with the COX-2 selective inhibiting compound include Myleran® (busulfan), Platinol® (cisplatin), Alkeran® (melphalan hydrochloride), Cytoxan® (cyclophosphamide), Leukeran® (chlorambucil), BiCNU® (carmustine), CeeNU® (lomustine [CCNU]) and Mustargen® (mechloroethamine hydrochloride). Examples of antibiotics that may be used in conjunction with the COX-2 selective inhibiting compound include Adriamycin® (doxorubicin hydrochloride), Blenoxane® (bleomycin sulfate), Cerubidine® (daunorubicin hydrochloride), Cosmegen® (dactinomycin), Mithracin® (plicamycin), Mutamycin® (mitomycin) and Novantrone® (mitoxantrone hydrochloride). Examples of hormones that may be used in conjunction with the COX-2 selective inhibiting compound include progesterone, estrogen, Estrace® (estradiol), DES and the like. Examples of anti-hormones that may be used in conjunction with the COX-2 selective inhibiting compound include Casodex® (bicalutamide), Eulexin® (flutamide) and Nilandrone® (nilutamide). Examples of LHRH analogs include Synarel® (nafarelin acetate), Lupron® (leuprolide acetate), Zoladex® (goserelin acetate) and Histerelin®. Examples of LHRH antagonists include ganirelix , cetrorelix and aberelix. Examples of anti-metabolites that may be used in conjunction with the COX-2 selective inhibiting compound include Cytosar® (cytarabine), Fludura® (fludarabine phosphate), Leustatin® (cladribine), methotrexate, Purinethol® (mercaptopurine), thioguanine and the like. Examples of monoclonal antibodies that may be used in conjunction with COX-2 selective inhibiting compound include Herceptin® (Trastuzumab). Examples of topoisomerase I inhibitors that may be used in conjunction with the COX-2 selective inhibiting compound include Camptosar® (irinotecan hydrochloride) and Hycamtin® (topotecan hydrochloride). Examples of topoisomerase II inhibitors that may be used in conjunction with the COX-2 selective inhibiting compound include Vepesid® (etoposide) and Vumon® (teniposide). Examples of miscellaneous anti-neoplastics that can be used in conjunction with the COX-2 selective inhibiting compound include Celestone® (betamethasone), DTIC® (dacarbazine), Elspar® (asparaginase), Gemzar® (gemcitabine hydrochloride), Hexalen® (altretamine), Hycamtin® (topotecan hydrochloride), Hydrea® (hydroxyurea), interferon A, Navelbine® (vinorelbine tartrate), Oncaspar® (pegaspargase), Oncovin® (vincristine sulfate), Proleukin® (aldesleukin), Rituxan® (rituximab), Rimaxin®, Taxol® (paclitaxel), Taxotere(® (docetaxel), Emcyt® (estramustine phosphate sodium), Velban® (vinblastine sulfate) and the like.

All conventional anti-cancer agents are used in conjunction with the COX-2 selective inhibitor at conventional doses that are determined by the skilled clinician. These compounds are known and normal daily dosages are well established. Typically, the individual daily dosages for these combinations may range from about one-fifth of the minimally recommended clinical dosages to the maximum recommended levels for the entities when they are given alone. Precise dosages are left to the discretion of the physician.

The COX-2 selective inhibitor rofecoxib is administered at a dosage that is effective for treating or preventing prostate cancer, generally within the daily dose range of about 5 mg to about 1000 mg, more particularly about 10 mg to about 500 mg per day, and even more particularly about 12.5 mg to about 100 mg per day.

The COX-2 selective inhibitor may be administered alone or in combination with the other active agents, via oral, parenteral (e.g., intramuscular, intraperitoneal, intravenous or subcutaneous injection, or implant), nasal, vaginal, rectal, sublingual, or topical administration and can be formulated into dosage forms that are appropriate for the particular route of administration desired.

Solid dosage forms for oral administration include capsules, tablets, pills, powders and granules. In solid dosage forms, the active compound is typically admixed with at least one inert pharmaceutically acceptable carrier such as sucrose, lactose or starch. Such dosage forms can also comprise, as is normal practice, additional substances other than inert diluents, e.g., lubricating agents such as magnesium stearate. Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. In the case of capsules, tablets and pills, the dosage forms may also comprise buffering agents.

When the dosage form is a capsule, it may contain, in addition to the materials noted above, a liquid carrier such as fatty oil. Various other materials may be present as coatings or to otherwise modify the physical form of the dosage unit. Tablets and pills can additionally be prepared with enteric coatings and tablets may be coated with shellac, sugar or both.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents. A syrup or elixir may contain the active compound, sucrose as a sweetening agent, methyl and propyl parabens as preservatives, a dye and a flavoring such as cherry or orange flavor.

Preparations according to this invention for parenteral administration include sterile aqueous or non-aqueous solutions, suspensions, or emulsions. Sterile compositions for injection may be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like may be incorporated as required. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The composition may contain the COX-2 selective inhibiting compound and the anti-cancer agent or agents, in combination with a pharmaceutically acceptable carrier.

The dosage of active ingredient in the compositions of this invention may be varied, however, it is necessary that the amount of the active ingredients be such that a suitable dosage form is provided. The selected dosage depends upon the desired effect, on the route of administration and on the duration of the treatment. The dose will vary from patient to patient depending upon the nature and severity of disease, the patient's weight, special diets then being followed by a patient, concurrent medications that are being used, and other factors which those skilled in the art will recognize. Based upon the foregoing, precise dosages are left to the discretion of the skilled clinician.

Methods of making the COX-2 selective inhibiting compound are well understood from the patent literature. For example, the compound useful herein and methods of synthesis are disclosed in U.S. Pat. No. 5,474,995 granted on Dec. 12, 1995. This publication is incorporated by reference. The compound rofecoxib has a known chemical structure.

While the invention has been described with reference to certain particular embodiments thereof, those skilled in the art will appreciate that various modifications may be made without departing from the spirit and scope of the invention. The scope of the appended claims is not to be limited to the specific embodiments described.

What is claimed is:

1. A method of treating or preventing prostate cancer in a male mammalian patient in need thereof, comprising administering to said patient a COX-2 selective inhibiting compound in an amount that is effective to treat or prevent prostate cancer, wherein the COX-2 selective inhibiting compound is rofecoxib.

2. A method of treating or preventing prostate cancer in accordance with claim 1 wherein the patient is a human.

3. A method in accordance with claim 1 further comprising administering to the patient a 5-alpha reductase inhibitor.

4. A method in accordance with claim 1 wherein the 5-alpha reductase inhibitor is selected from the group consisting of: finasteride, dutasteride and epristeride.

5. A method of treating or preventing prostate cancer in a male mammalian patient comprising administering to the patient rofecoxib in combination with radiation therapy.

6. A method in accordance with claim 5 wherein the radiation therapy comprises external radiation or radioactive seed implantation.

7. A method of treating or preventing prostate cancer in accordance with claim 1 wherein the COX-2 selective inhibiting compound is administered in combination with selenium.

8. A method of treating or preventing prostate cancer in accordance with claim 1 wherein the COX-2 selective inhibiting compound is administered in combination with vitamin C or E.

9. A method of treating or preventing prostate cancer in accordance with claim 1 wherein the COX-2 selective inhibiting compound is administered in combination with at least one drug selected from the group consisting of:
alkylating agents, antibiotics, hormones, anti-hormones, LHRH analogs and antagonists, anti-metabolites and miscellaneous anti-cancer agents.

10. A method of treating or preventing prostate cancer in accordance with claim 9 wherein the COX-2 selective inhibiting compound is administered in combination with at least one drug selected from the group consisting of:
Myleran® (busulfan), Platinol® (cisplatin), Alkeran® (melphalan hydrochloride), Cytoxan® (cyclophosphamide), Leukeran® (chlorambucil), BiCNU® (carmustine), CeeNU® (lomustine [CCNU]), Mustargen® (mechloroethamine hydrochloride), Adriamycin® (doxorubicin hydrochloride), Blenoxane® (bleomycin sulfate), Cerubidine® (daunorubicin hydrochloride), Cosmegen® (dactinomycin), Mithracin® (plicamycin), Mutamycin® (mitomycin), Novantrone® (mitoxantrone hydrochloride), progesterone, estrogen, Estrace® (estradiol), DES, Casodex® (bicalutamide), Eulexin® (flutamide), Nilandrone® (nilutamide), Synarel® (nafarelin acetate), Lupron® (leuprolide acetate), Zoladex® (goserelin acetate), Histerelin®, ganirelix, cetrorelix, aberelix, Cytosar® (cytarabine), Fludura® (fludarabine phosphate), Leustatin® (cladribine), methotrexate, Purinethol® (mercaptopurine), thioguanine, Camptosar® (irinotecan hydrochloride), Celestone® (betamethasone), DTIC® (dacarbazine), Elspar® (asparaginase), Gemzar® (gemcitabine hydrochloride), Hexalen® (altretamine), Hycamtin® (topotecan hydrochloride), Hydrea® (hydroxyurea), interferon A, Navelbine® (vinorelbine tartrate), Oncaspar® (pegaspargase), Oncovin® (vincristine sulfate), Proleukin® (aldesleukin), Rituxan® (rituximab), Rimaxin®, Taxol® (paclitaxel) and Velban® (vinblastine sulfate).

* * * * *